United States Patent [19]

Murphy-Chutorian

[11] Patent Number: 5,693,041
[45] Date of Patent: Dec. 2, 1997

[54] LASER DELIVERY MEANS RING STABILIZATION METHOD AND APPARATUS FOR SURGICAL AND OTHER PROCEDURES

[75] Inventor: Douglas R. Murphy-Chutorian, Sunnyvale, Calif.

[73] Assignee: Eclipse Surgical Technologies, Inc., Sunnyvale, Calif.

[21] Appl. No.: 702,264

[22] Filed: Aug. 23, 1996

[51] Int. Cl.$^6$ ................................................. A61B 17/36
[52] U.S. Cl. ................................................. 606/2; 606/16
[58] Field of Search ........................... 606/2, 10–16, 606/49; 607/88, 89

[56] References Cited

U.S. PATENT DOCUMENTS

| | | |
|---|---|---|
| 4,658,817 | 4/1987 | Hardy . |
| 5,125,923 | 6/1992 | Tanner et al. ............... 606/12 |
| 5,125,926 | 6/1992 | Rudko et al. . |
| 5,242,440 | 9/1993 | Shippert ..................... 606/49 |
| 5,380,316 | 1/1995 | Aita et al. . |
| 5,389,096 | 2/1995 | Aita et al. . |

FOREIGN PATENT DOCUMENTS 0070459  1/1983  European Pat. Off. .

OTHER PUBLICATIONS

Deckelbaum, "Cardiovascular Apps. of Laser Tech.", Lasers in Surgery and Medicine, 15:315–341 (1994).
Frazier et al., "Myocard. Revasc. with Las.", Cullen Cardio. Res. Labs., Tx. Heart Inst., Supp. II C vol. 92, No. 9, II-58–65 (Nov. 1, 1995).

Primary Examiner—Jennifer Bahr
Assistant Examiner—Bryan K. Yarnell
Attorney, Agent, or Firm—Ray K. Shahani; Janet K. Castaneda

[57] ABSTRACT

An apparatus for stabilizing a laser delivery device used during a surgical procedure by securing the laser delivery device to a surgeon's hand is defined by a finger mounting portion for securing at least one laser delivery device to at least one of the surgeon's fingers, and laser delivery device guide attached to the finger mounting portion for directing laser energy from the distal end of the laser delivery means. The finger mounting portion has at least one ring portion for removably encircling the surgeon's finger(s). Embodiments of the guide orient the laser delivery device either axially or trans-axially at a predetermined angle. The guide may be tubular with a preselected curvature, or tubular and adjustable so as to orient the laser delivery device into a plurality of positions. A locking mechanism couples the laser delivery device to the guide and rotating the guide may orient the laser delivery means into a plurality of predetermined positions. Laser delivery/fiber advance interlock mechanisms may be provided to prevent unintentional delivery of laser energy and unintentional advancement of the laser delivery device. A web-shaped guide means fits between and is secured to the surgeon's fingers and may have one or more aperture for guiding the laser delivery device.

35 Claims, 6 Drawing Sheets

1

LASER DELIVERY MEANS RING STABILIZATION METHOD AND APPARATUS FOR SURGICAL AND OTHER PROCEDURES

FIELD OF THE INVENTION

The present invention relates to surgical procedures involving laser energy using fiber optic and other laser delivery systems. More particularly, the invention is a method and apparatus for performing a surgical procedure using a laser delivery means mounted directly onto a surgeon's one or more fingers with a laser delivery means stabilization apparatus, thereby providing low-profile, uncomplicated, efficacious, versatile and safe apparatus and method, particularly in laser-assisted transmyocardial revascularization (TMR).

BACKGROUND OF THE INVENTION

The recent expansion in the range of applications for lasers in medicine has been limited, in part at least, by the relatively few types of apparatus available to the surgeon. In particular, with regard to minimally invasive surgical procedures, maneuvering laser delivery system such as fiber optic tools and other types of laser waveguides in small spaces while manipulating visualization and other adjunct devices, presents an increased risk by the use of laser energy. In the operating room, tools used for delivery of laser energy need to be controlled as much as possible regardless of the application, to prevent injury to the patient, personnel and other equipment if fired improperly such as in the wrong direction or if a tool is dropped during it's use.

In the treatment of heart disease, one surgical method of improving myocardial blood supply is called transmyocardial revascularization (TMR), the creation of channels from the epicardial to the endocardial portions of the heart. The procedure using needles in a form of "myocardial acupuncture" has been used clinically since the 1960s. Deckelbaum. L. I., Cardiovascular Applications of Laser technology, *Lasers in Surgery and Medicine* 15:3 15–341 (1994). The technique relieves ischemia by allowing blood to pass from the ventricle through the channels either directly into other vessels perforated by the channels or into myocardial sinusoids which connect to the myocardia/microcirculation. Thus transformed human heart resembles that of a reptile.

In the reptilian heart, perfusion occurs via communicating channels between the left ventricle and the coronary arteries. Frazier, O. H., Myocardial Revascularization with Laser—Preliminary Findings, *Circulation*, 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR using lasers to bore channels in the myocardium. Histological evidence of probable new vessel formation adjacent to collagen occluded transmyocardial channels exists. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the lumen of the laser channels is or can become hemocompatible and that it resists occlusion caused by thrombo-activation and or fibrosis. A thin zone of charring occurs on the periphery of the laser-created transmyocardial channels through the well-known thermal effects of optical radiation on cardiovascular tissue.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforates a portion of tissue to provide the laser beam direct access to distal tissue.

U.S. Pat. Nos. 5,380,316 issued Jan. 10, 1995 and 5,389,096 issued Feb. 14, 1995 both to Aita et al. teach, respectively, systems and methods for intra-operative and percutaneous myocardial revascularization. The '316 patent is related to TMR performed by inserting a portion of an elongated flexible lasing apparatus into the chest cavity of a patient and lasing channels directly through the outer surface of the epicardium into the myocardium tissue. In the '096 patent TMR is performed by guiding an elongated flexible lasing apparatus into a patient's vasculature such that the firing end of the apparatus is adjacent the endocardium. Channels are created directly through the endocardium into the myocardium tissue without perforating the pericardium layer.

To date, problems encountered by surgeons in performing TMR include difficult physical access to portions of the heart, including the posterior and inferior aspects, without causing undesired trauma to the chest and thoracic cavity.

Thus, it is an advantage of the present invention to provide a laser delivery means ring stabilization method and apparatus for surgical procedures.

It is a further advantage of the present invention to provide an apparatus which fits onto one or more fingers of a surgeon's hand, thus eliminating any risk of accidental slipping or dropping the laser delivery tool or tools during the procedure.

It is a further advantage of the present invention to provide an apparatus which has a low physical profile, thereby permitting access to the heart through a minimally-sized aperture in the chest wall to perform heart surgery, including TMR, and other procedures in cardiology.

It is a further advantage of the present invention to provide an apparatus which is adaptable for directing laser energy as desired, even while performing a procedure such as TMR in inaccessible regions of the heart, including the posterior and inferior regions.

It is a further advantage of the present invention to provide an apparatus which secures the fiber optic or other laser delivery system or means directly to the surgeon's fingers, thus leaving the remainder of the surgeon's fingers and hand to manipulate the heart or other structure being treated or adjacent to areas being treated.

It is a further advantage of the present invention to provide an apparatus which eliminates the risk of accidental delivery of laser energy to the surgeon's hands, other equipment or attendants during the procedure.

SUMMARY OF THE INVENTION

A laser delivery means ring stabilization apparatus is described which comprises a finger mounting portion which resembles a ring or band with a laser delivery device guide means. The guide means is fixedly or adjustably attached to the finger mounting portion so as to direct the laser delivery means either forward, i.e. essentially parallel with or in the same axial direction as the central axis of the finger or fingers to which the apparatus is mounted, downward, i.e. essentially perpendicular to the central axis, or at some other angle with regard to the central axis. In a preferred embodiment, the guide means has a straight, curved or bent tubular shape. A preferred embodiment of the guide means comprises a fiber locking system. In another preferred embodiment, an indexed, rotating guide means allows the surgeon to select the direction in which the laser delivery means is oriented with respect to the surgeon's fingers.

A laser delivery means ring stabilization apparatus which mounts onto a plurality of fingers is also described. A guide portion directs the laser delivery means in one or more directions, i.e. through one or more guiding apertures, with respect to the central axis of the fingers to which the apparatus is mounted. A preferred embodiment includes a finger or thumb actuated fiber advance mechanism. This type of system provides the surgeon with a low-profile, easily positionable device which allows efficient and safe revascularization of the myocardium.

Another preferred embodiment comprises either, or both, a laser energy delivery interlock and a fiber advance interlock. Advancement of the fiber, bundle or other laser delivery means is prevented until and unless the distal tip of the guide portion or other guide means is positioned against the epicardial surface of the heart adjacent the preselected portion of myocardium to be treated. Switch means include but are not limited to spring loaded electrical contacts, resistance sensors and optical sensors.

Essentially all of the preferred embodiments of the present invention secure the fiber optic tool or other laser delivery device to the surgeon's hand while permitting use of the same hand and fingers for manipulating structures, including the heart, at or adjacent the surgical site.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Figure 1:
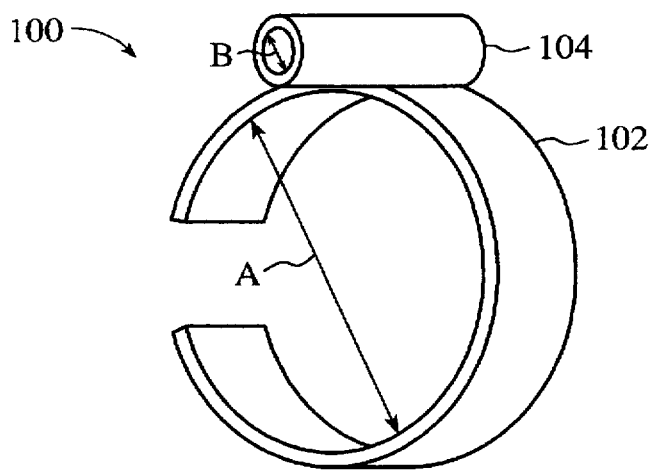
FIG. 1 is a representative perspective view of a preferred embodiment of a laser delivery means ring stabilization apparatus of the present invention.

FIG. 1 is a representative perspective view of a preferred embodiment of a laser delivery means ring stabilization apparatus of the present invention. The apparatus 100 is comprised of essentially two parts, a ring portion 102 or other finger mounting means, and a guide means 104. The finger mounting means is a flexible or rigid ring, circular band, partial ring, band, clip, adhesive, etc. Other means for attaching the apparatus securely to the surgeon's fingers will be known to those skilled in the art and are included with in the scope of this invention. The inside diameter of the ring A will be made appropriate for secure placement on the gloved finger of the surgeon or other operator of the apparatus. The guide means consists of a short barrel or tubular shaped member. The inside diameter B of the guide means will be selected to operatively guide a laser delivery means through the guide. It will be understood that typical laser delivery means include single optical fibers, fiber bundles, fiber optic devices and other laser energy waveguides. The guide means can be attached permanently or removably.

It is understood that while one embodiment of the guide means is essentially a short, tubular section, it could be replaced with a snap, hook, two-piece hinged collar, cuff or other guide means which would couple to (or wrap around) the optic cable or other laser delivery means. A variety of embodiments will be apparent to those skilled in the art. An important function of these embodiments is to accept a fiber optic device with a large fitting at the distal end, such as a side-angle firing tip. A wide variety of firing tips, side firing or otherwise, as well as numerous other devices for internal or catheter procedures are available. Since it is impossible to insert many different types of devices through a narrow, hollow, tubular guide means with a limited inside diameter, these alternate embodiments are of great utility to effectively allow insertion and guidance of any suitable laser delivery means.

Figure 2A:
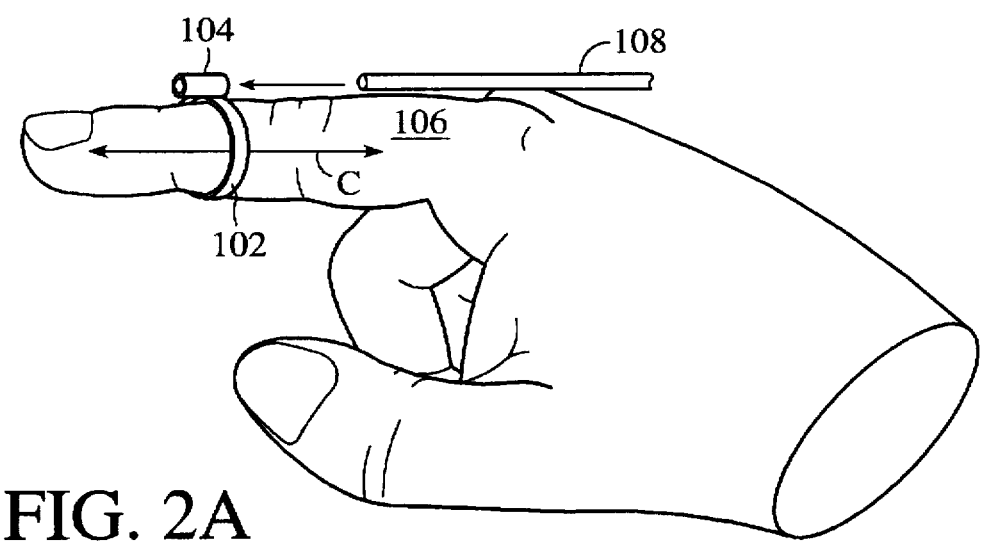
FIG. 2A is a representative perspective view of a preferred embodiment of the method of use of an axially oriented guide means laser delivery means ring stabilization apparatus of the present invention.

FIG. 2A is a representative perspective view of a preferred embodiment of the method of use of an axially oriented laser delivery means ring stabilization apparatus of the present invention. As shown, once the ring portion 102 of the apparatus is placed over the surgeon's finger 106, the central axis C of the apparatus is defined by an axis perpendicular to the circular cross-section of the ring portion. As shown for representative purposes, the central axis is essentially parallel to the surgeon's fully extended finger. However, it is understood that the surgeon's finger will not necessarily be extended at all times—the surgeon can use his or her fingers to hold and otherwise manipulate the heart, other body parts either internal or external, or other tools. Thus, the surgeon's fingers may be fully extended, closed tightly, or in another position. Thus, guide means 104 is oriented in such a position as to direct a fiber extending therethrough in a direction substantially parallel to the central axis of the ring apparatus. It will be understood that since the orientation of the tubular guide means can be selected during manufacture, the direction which the guide means directs the optical fiber can be varied from a parallel to the axis to some other angle.

Figure 2B:
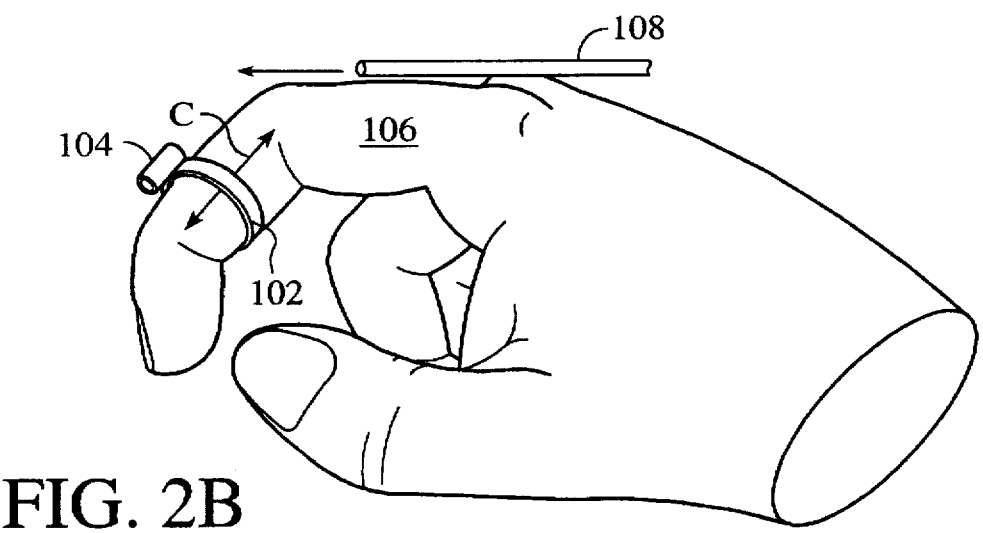
FIG. 2B is a representative perspective view of a preferred embodiment of the method of use of an axially oriented guide means laser delivery means ring stabilization apparatus of the present invention.

FIG. 2B is a representative perspective view of a preferred embodiment of the method of use of an axially oriented guide means laser delivery means ring stabilization apparatus of the present invention. In this view, the apparatus is essentially identical to that shown in FIG. 2A, however, the finger of the surgeon is bent downward. Thus, laser energy can be directed downward at an angle to the remaining fingers and palm of the hand.

Figure 3:
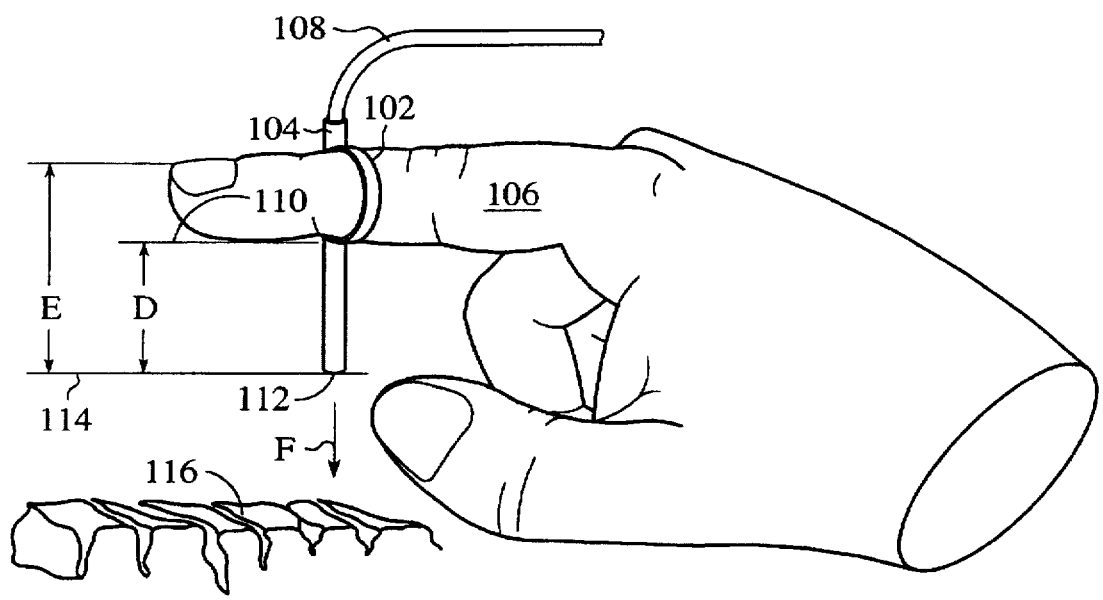
FIG. 3 is a representative perspective view of a preferred embodiment of a trans-axially oriented guide means laser delivery means ring stabilization apparatus of the present invention.

FIG. 3 is a representative perspective view of a preferred embodiment of a trans-axially oriented laser delivery means ring stabilization apparatus of the present invention. As shown, guide means 104 is attached to finger mounting ring 102 in such position that fiber 108 or other laser delivery means extends through the guide means 104 in a direction substantially perpendicular to the central axis C of the apparatus as well as to the mostly extended fingers of the surgeon. In this embodiment, the fiber 108 is positioned to one side of the surgeon's finger 106. The fiber extends a distance D past the lower surface 110 of the finger. Once the distal tip 112 of the fiber is placed in contact with epicardial surface 114 of the heart, delivery of laser energy can commence. As laser energy is delivered, the finger is moved toward the surface of the heart in direction E at an operative rate. With the fiber 108 fixed rigidly within guide means 104, the finger can move through a distance D but, in general, not farther, thus ensuring a maximum depth of penetration of TMR channel into myocardium 116. Alternatively, the fiber 108 can be placed slidably through tubular guide means 104. Once the distal tip 112 of the fiber is placed in contact with epicardial surface 114, the fiber can be advanced in direction F. In the present embodiment, as in those contemplated herein, it will be understood that the surgeon's fingers will be in contact with the beating heart, holding the apparatus in place over the epicardial surface.

Figure 4:
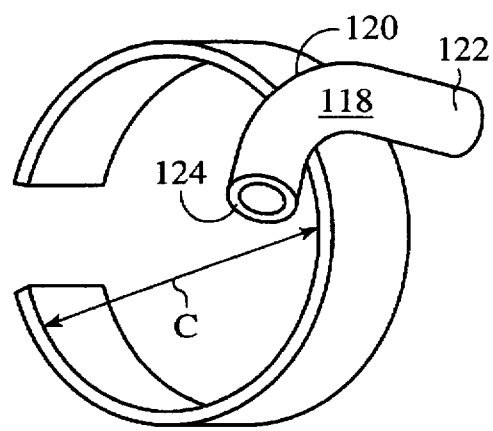
FIG. 4 is a representative perspective view of another preferred embodiment of a trans-axially oriented guide means laser delivery means ring stabilization apparatus of the present invention.

FIG. 4 is a representative perspective view of another preferred embodiment of a trans-axially oriented, laser delivery means ring stabilization apparatus of the present invention. As shown, tubular guide means 118 has a central bend or curvature 120 located at a point between the proximal end 122 and the distal end 124. The apparatus can be slipped over the finger with the guide means mounted on the upper surface 116 of the surgeon's finger with the fiber directed toward the right of the central axis C, as shown, or the apparatus can be worn with the guide means on one side, deflecting the fiber to a downward position. It will be understood that the range in degree of curvature of the bend in the guide means 118 may be limited by a maximum bend radius for a particular laser delivery fiber optic or bundle system. Consideration must also be given to the laser delivery system's ability to slide through the guide means if necessary.

Figure 5A:
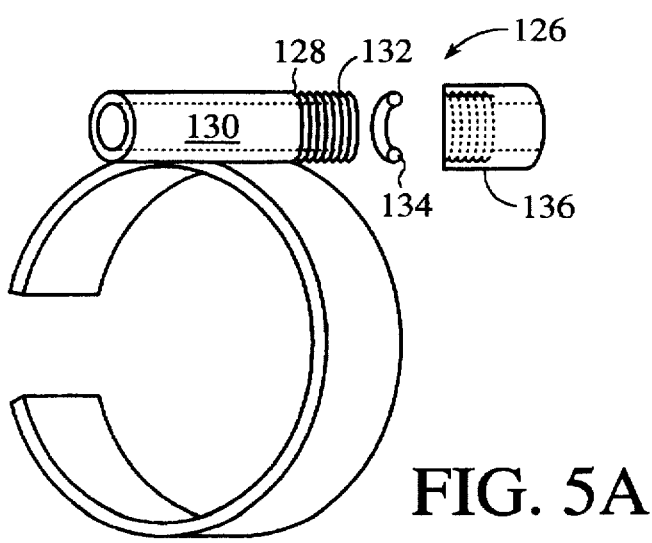
FIG. 5A is a representative perspective view of a preferred embodiment of a laser delivery means ring stabilization apparatus of the present invention with laser delivery means locking means.

FIG. 5A is a representative perspective view of a preferred embodiment of a laser delivery means ring stabilization apparatus of the present invention with laser delivery means locking means. As described, the various embodiments of the present invention can be utilized with a manual or an automatic fiber advance mechanism. In either case, it is often desirable to secure or lock the fiber into position, or to secure a clamp or other device to the fiber itself. In such case, fiber locking assembly 126 has particular utility. The proximal end 128 of the guide means 130 has a threaded portion 132, an O-ring 134, and a cap portion 136. It will be understood that once the assembly is threaded together and tightened slightly, the threaded portion and O-ring will become compressed around the fiber extending therethrough, thus fixing the fiber at a predetermined position within the guide means.

Figure 5B:
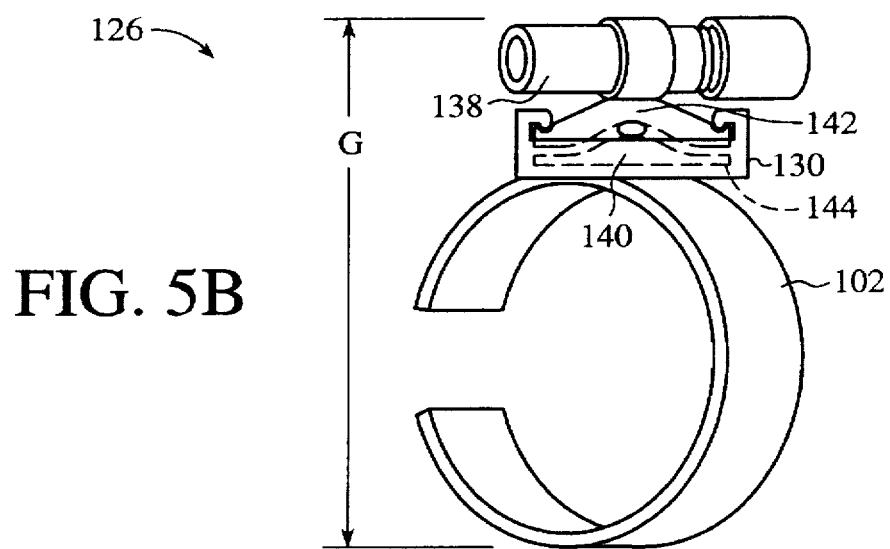
FIG. 5B is a representative perspective view of a preferred embodiment of a laser delivery means ring stabilization apparatus of the present invention with rotating guide means.

FIG. 5B is a representative perspective view of a preferred embodiment of a laser delivery means ring stabilization apparatus of the present invention with rotating guide means. The ring portion 102 has a rotating guide means 138 with a locking assembly 126. The rotating guide means is also comprised of a stationary lower body portion 140 attached to the finger mounting means 102, and an upper body portion 142 which rotates to a plurality of trans-axial directions. A preferred embodiment comprises a Belville washer 144 or other means to provide compression, maintain a low profile and minimize overall apparatus height G. Detents, grooves and notches or other systems provide indexed action such that predetermined angular orientations, for example two (2) spaced 90°, or six (6) spaced at 15°, can be selected and maintained conveniently by the surgeon or as a pre-set option. It will be apparent to those skilled in the art that rotation of the guide means can be achieved in a number of different embodiments, including but not limited to bearings, etc., all of which will be included within the scope of the present invention.

Figure 6A:
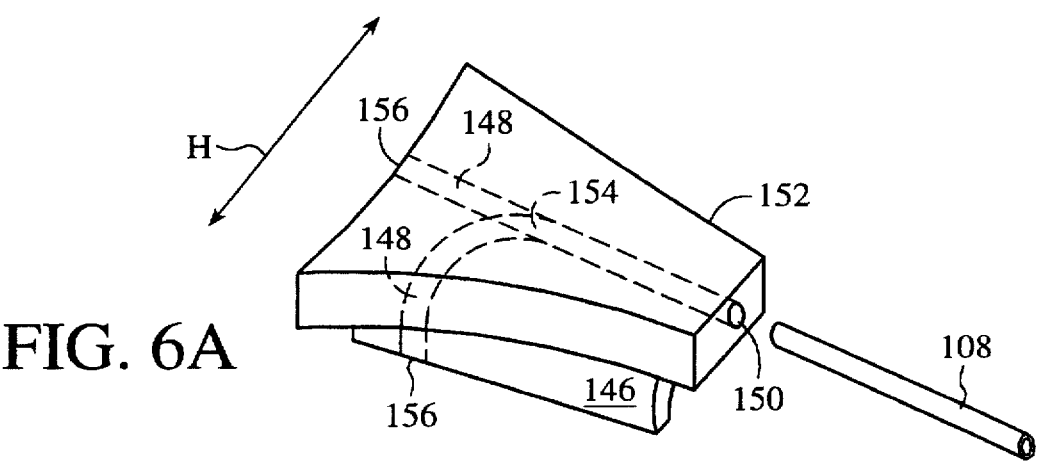
FIG. 6A is a representative perspective view of a preferred embodiment of a laser delivery means multiple finger ring stabilization apparatus of the present invention.

FIG. 6A is a representative perspective view of a preferred embodiment of a laser delivery means multiple finger ring stabilization apparatus of the present invention. The apparatus operates by guiding an optical fiber 108 or other laser delivery device between the surgeon's fingers. Web-shaped guide means 146 has a plurality of fiber paths 148 defined by one or more openings 150 at the proximal end 152, optionally branching at a certain point 154, and extending through to the distal ends 156 of the paths. It will be understood that the channels may branch from a single opening, as shown, or a plurality of non-communicating fiber paths can be placed through the guide means 146, each with individual or mutual locking means and advancement means as desired.

Figure 6B:
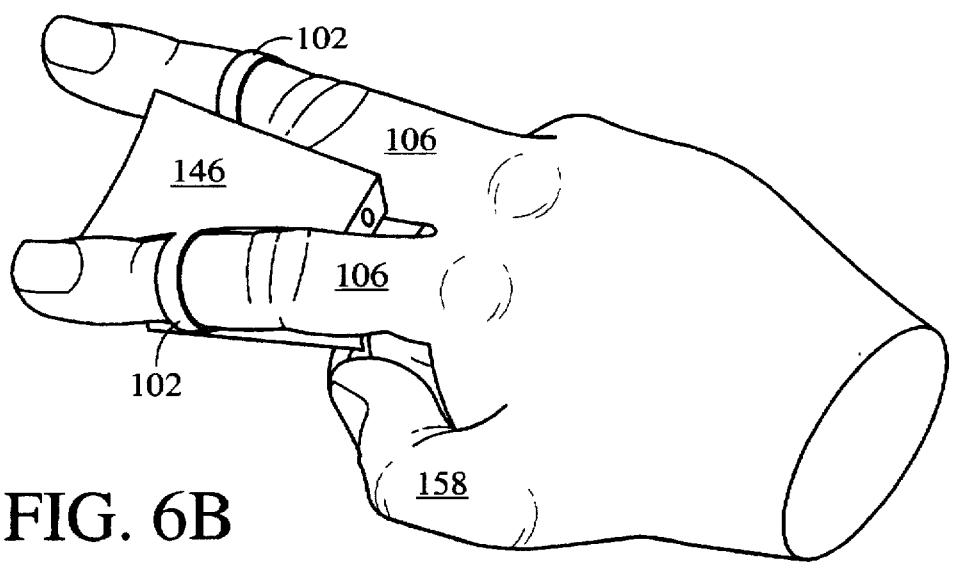
FIG. 6B is a representative perspective view of a preferred embodiment of a method of use of a laser delivery means multiple finger ring stabilization apparatus of the present invention.

FIG. 6B is a representative perspective view of a preferred embodiment of a method of use of a laser delivery means multiple finger ring stabilization apparatus of the present invention. As described, the apparatus is fitted between the surgeon's fingers on two finger mounting ring portions 102. In the present embodiment, an extremely low profile can be achieved since the overall operating height H for the instrument can be as little as the actual profile depth of the space between the surgeon's fingers. The surgeon's throb 158, other fingers and the fingertips are left free to serve other functions, including but not limited to holding, rotating or otherwise manipulating the heart, positioning the apparatus, etc. It will be understood that the present invention enhances the efficacy and safety of conventional methods and apparatus for performing laser-assisted TMR. By feeding the laser delivery device through the web-shaped guide means 146, the risk of harm to personnel is removed and the increased control for precisely performed TMR heretofore unavailable and impossible is provided to the surgeon.

Figure 7A:
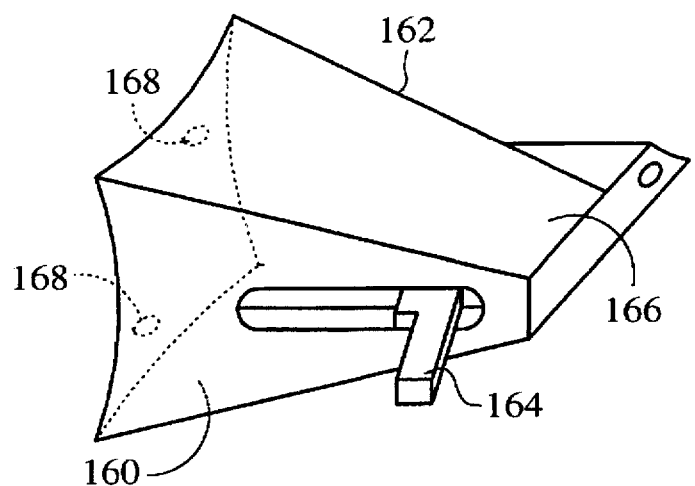
FIG. 7A is a representative perspective view of a preferred embodiment of a laser delivery means multiple finger ring stabilization apparatus of the present invention with finger actuated fiber advance means.

FIG. 7A is a representative perspective view of a preferred embodiment of a laser delivery means multiple finger ring stabilization apparatus of the present invention with finger actuated fiber advance means. Extending from the lower surface 160 of a preferred embodiment of the web-shaped guide means 162 is a thumb-activated fiber advance lever 164 located adjacent the proximal end 166 of the apparatus. It will be understood that the surgeon's fingers 106 are prevented from being positioned at any point near the distal ends 168 of the fiber guide paths, thus eliminating risk of harm to the surgeon.

Figure 7B:
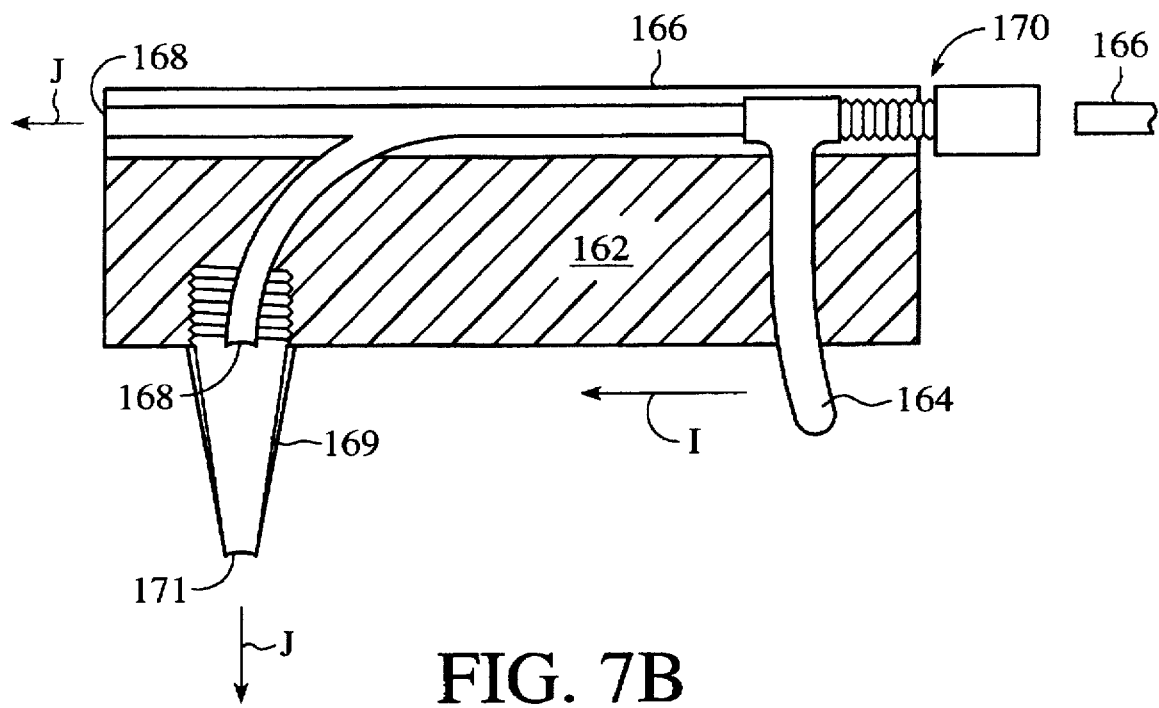
FIG. 7B is a representative cross section view of a preferred embodiment of a laser delivery means multiple finger ring stabilization apparatus of the present invention with finger actuated fiber advance means and distally located tissue piercing means.

FIG. 7B is a representative cross section view era preferred embodiment era laser delivery means multiple finger ring stabilization apparatus of the present invention with finger actuated fiber advance means and distally located tissue piercing means. As described, in a preferred embodiment when optical fiber 108 is inserted into the apparatus it will need to be locked onto the apparatus with fiber locking means 170 for the fiber advance mechanism to operate. Thus, as the lever 164 is moved toward the distal end of the apparatus in direction I, the fiber or fibers or other laser delivery means are moved in direction J. Such fiber advance means are more fully disclosed in co-pending U.S. patent application Ser. No. 08/627,701 filed Mar. 29, 1996 and Ser. No. 08/675,698 filed Jul. 3, 1996.

A preferred embodiment of the present invention is provided with a piercing tip 169 or other piercing means. This piercing tip will create an initial perforation in the outer surface of the tissue to be revascularized or otherwise treated. With regards to TMR, perforation of the epicardium can be achieved with the piercing tip. Thereafter, the fiber 108 can be advanced therethrough. The piercing tip 169 will assist the surgeon in stabilizing the ring apparatus during the procedure. Once the surface of the tissue is pierced, the distal tip 171 of the piercing means will stay in place, buried slightly into the tissue to be treated. It will be understood that the distal end 171 of the piercing means 169 may define a circular opening either parallel with the lower surface 160 of the web shaped guide means 162 or at an operative piercing angle to the lower surface. A preferred embodiment of the tissue piercing tip 169 has a heating element or other heating means disposed therein. The heating means will aid in piercing the tissue and preventing undesired bleeding from the perforation in the tissue. Another embodiment of the tissue piercing means is extendable and retractable. This embodiment permits the surgeon to glide the lower surface 160 of the guide means over the surface of the tissue to be treated unit the precise position for treatment is reached. At that point, the tissue piercing tip can be extended and the tissue pierced, followed by subsequent advancement of the fiber for laser delivery. Once the tissue has been treated, the fiber 108 and piercing tip 169 may be retracted for relocation of the guide means. Alternatively, once the tissue has been treated with the fiber, the fiber alone can be retracted and the guide means re-oriented with the tissue piercing tip in place, in a pivoting type of motion, to allow creation of another TMR channel originating from the initial point of perforation. It will be understood that in addition to delivery of laser energy, the apparatus can be used for visualization era certain portion of tissue, either at a surface or within a structure such as the heart. It will also be understood that if the tissue piercing tip 169 has a slight curvature, an optical fiber or other laser delivery means may be advanced through the tip at an angle to the lower surface 160 of the guide means. Thereafter, rotation of the tissue piercing tip 169 will permit creation era second TMR channel originating from the initial point of perforation. Such tissue piercing means are more fully disclosed in co-pending U.S. patent applications Ser. No. 08/675,698 filed Jul. 32, 1996 and No. 675,732 filed Jul. 3, 1996.

Figure 8A:
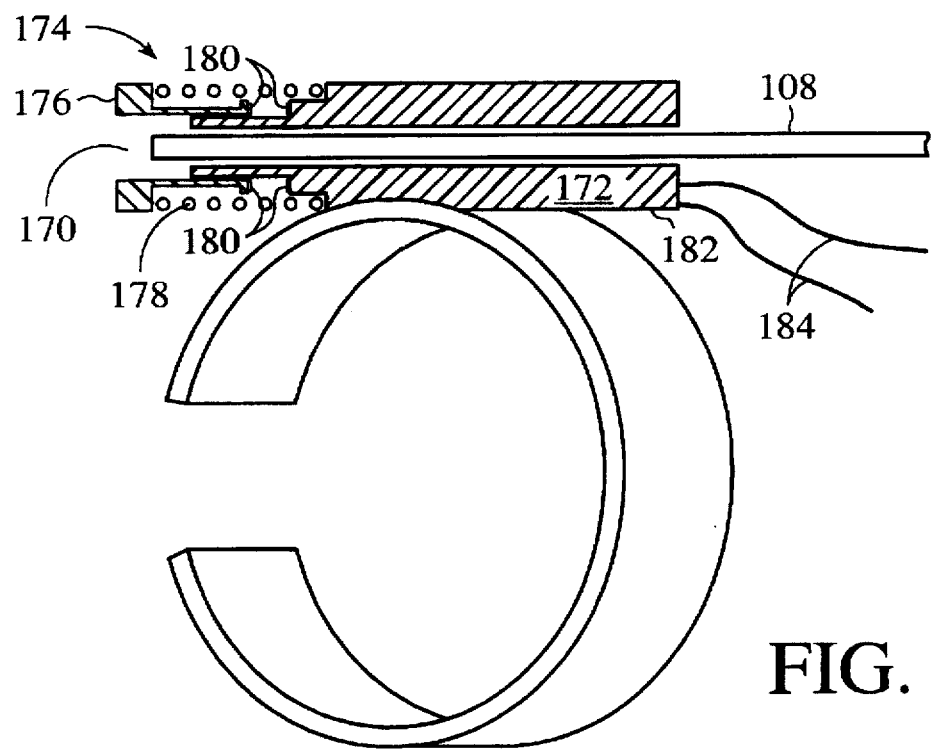
FIG. 8A is a representative perspective view of a preferred embodiment of a laser delivery means ring stabilization apparatus of the present invention with laser delivery and fiber advance interlock means comprising a spring-biased electrical contact-type switch means.

FIG. 8A is a representative perspective view of a preferred embodiment of a laser delivery means ring stabilization apparatus of the present invention with laser delivery/fiber advance interlock means comprising a spring-biased electrical contact-type switch means. Mounted on the distal end 170 of the guide means 172, laser delivery/fiber advance interlock means 174 comprises a distal heart contact member 176, spring means 178 and electrical contacts 180 on both the heart contact member 176 and the distal end 170 of guide means 172. From the proximal end 182 of the guide means, electrical wiring 184 extends back to the laser control and fiber advance control means.

Figure 8B:
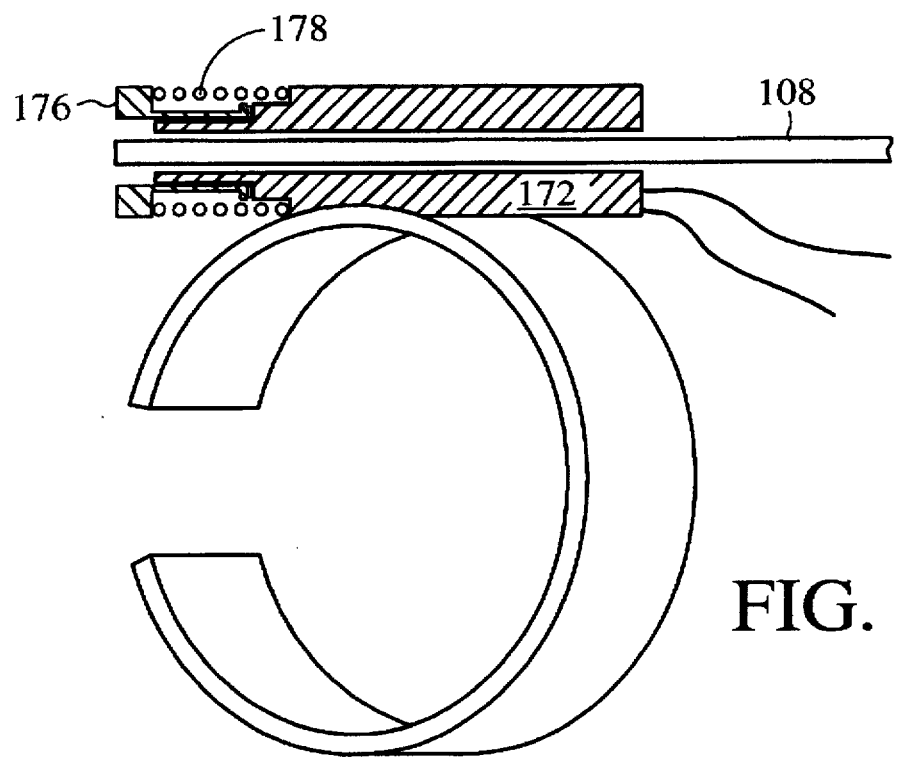
FIG. 8B is a representative detail view of a preferred embodiment of a laser delivery/fiber advance interlock means of the present invention comprising a spring-biased electrical contact-type switch means in a closed position.

FIG. 8B is a representative detail view era preferred embodiment era laser delivery and fiber advance interlock means of the present invention comprising a spring-biased electrical contact-type switch means in a closed position. It will be understood by those skilled in the art that various embodiments of the interlock assembly are possible and will be included within the scope of the present invention. In most embodiments, control schemes include laser delivery and interlock circuits and fiber advance and interlock circuits. By requiring an electrical contact signal formed by the closed circuit when the distal end of the guide means 170 is in contact with the hear contact portion 176 in contact with the epicardial surface (not shown), laser delivery and/or fiber 108 advance is prevented until and unless the apparatus is positioned intentionally and firmly in place. Timing delay circuit will prevent accidental or unintentional laser delivery or fiber advance. These embodiments are especially well suited for protecting the patient, the operating room and staff as well as the hands and fingers of the surgeon.

Figure 9:
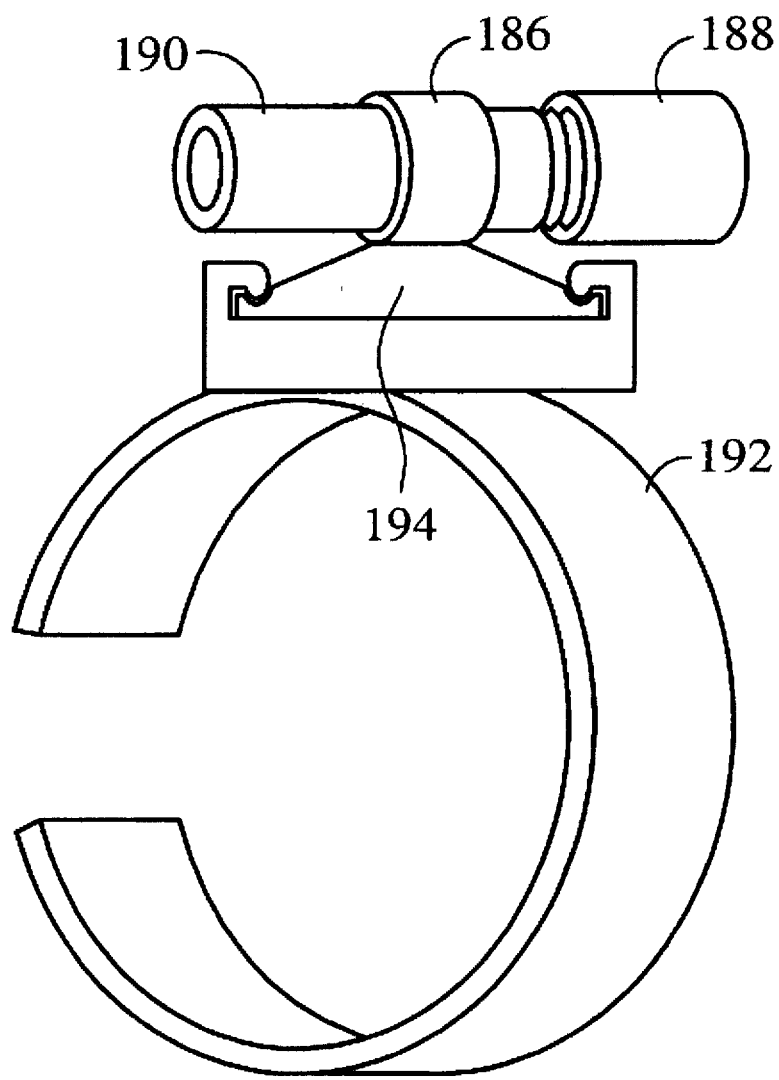
FIG. 9 is a representative perspective view of a preferred embodiment of a laser delivery means ring stabilization apparatus of the present invention with laser delivery means locking means, rotating guide means and laser delivery/fiber advance interlock means.

FIG. 9 is a representative perspective view of a preferred embodiment of a laser delivery means ring stabilization apparatus of the present invention with laser delivery means locking means, rotating guide means and laser delivery/fiber advance interlock means. The guide means 186, equipped with both fiber and laser delivery means locking means 188, and laser delivery and fiber advance interlock means 190, is mounted rotatably onto 192 with rotating means 194. Embodiments of fiber locking means, laser delivery/fiber advance means and rotation means will be known to those skilled in the art and are included within the scope of the present invention.

The present invention is intended for use with any medical laser. In particular, Holmium or excimer lasers are particularly well suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers, rods, mirror configurations, articulated arm waveguides and other laser delivery means. It will also be understood that the preferred embodiments of the apparatus and methods of the present invention as described herein including the novel combinations and use of any conventional mechanisms which are known to those skilled in the art are included within the scope of this invention.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. A hand surgical apparatus for securing a distal end of a laser delivery means operated from a remote laser device comprising:

a guide means defining a body having proximal and distal ends, the body having a length and width dimension no larger than a length and width dimension of the finger's of a surgeon's hand, the guide means: a) is connected to a finger mounting means, b) encompasses at least one fiber optical waveguide member which forms part of a laser delivery means and c) is adapted for directing laser energy outwardly from the distal end of the laser delivery means; and, a finger mounting means for attaching the guide means to at least one finger of a surgeon's hand, yet enabling movement of the at least one finger, wherein the finger mounting means has a central axis;

the guide means and the finger mounting means further determining orientation of the distal end of the laser delivery means effectuated by movement of the at least one finger, thereby stabilizing and providing precision aiming of the laser delivery means for an internal surgical procedure.

2. The apparatus of claim 1 in which the finger mounting means comprises at least one generally circular ring portion for removably encircling the at least one finger of the surgeon's hand, the central axis substantially perpendicular to the circular ring portion.

3. The apparatus of claim 1 in which the guide means secures the laser delivery means to the at least one finger of the surgeon's hand in a direction parallel to the central axis of the finger mounting means.

4. The apparatus of claim 1 in which the guide means secures the laser delivery means to the at least one finger of the surgeon's hand in a direction at an angle to the central axis of the finger mounting means.

5. The apparatus of claim 1 in which the guide means is tubular with a preselected curvature.

6. The apparatus of claim 1 in which the guide means is tubular and adjustable so as to orient the laser delivery means axially with respect to the central axis and into a plurality of positions at an angle to the central axis.

7. The apparatus of claim 1 further comprising a locking means for coupling the laser delivery means to the guide means.

8. The apparatus of claim 7 in which the locking means comprises an O-ring and a cap portion.

9. The apparatus of claim 7 in which the locking means is a closure for coupling the laser delivery means to the guide means.

10. The apparatus of claim 1 in which the guide means is rotatably attached to the finger mounting means.

11. The apparatus of claim 10 in which the rotating guide means is indexed so as to orient the laser delivery means into a plurality of positions with respect to the central axis.

12. The apparatus of claim 1 further comprising a fiber advance means and interlocking means attached to the guide means, the fiber advance means includes a finger manipulable member for translation of the at least one fiber optical waveguide member.

13. The apparatus of claim 12 wherein the interlocking means is for laser firing and fiber control that includes a distal heart contact member biased by a coaxial spring-biased electrical contact switch element that encompasses the at least one fiber optical waveguide member.

14. The apparatus of claim 1 wherein the guide means comprises a proximal end, a distal end, an upper surface, a lower surface and is generally web shaped such that the proximal end is adapted to fit between at least two fingers of the surgeon's hand adjacent a palm of the surgeon's hand while the distal end is disposed between the two fingers adjacent the surgeon's fingertips, the upper and the lower surfaces are essentially coplanar with the two fingers and the palm of the surgeon's hand, the guide mean further comprising at least one aperture extending from the proximal end there through to the distal end for guiding the laser delivery means.

15. The apparatus of claim 14 wherein at least one of the at least one apertures terminates at the distal end of the guide means.

16. The apparatus of claim 14 wherein at least one of the at least one aperture terminates at the lower surface of the guide means.

17. The apparatus of claim 14 wherein the guide means comprises at least two apertures, at least one of the apertures terminating adjacent the distal end of the guide means, and at least one of the apertures testing in the lower surface of the guide means.

18. The apparatus of claim 14 further comprising fiber advance means attached to the guide means, the advance means includes a finger manipulable member for translation of the at least one fiber optical waveguide member through the guide means.

19. The apparatus of claim 14 in which the fiber advance means further comprises a fiber locking means for maintaining the at least one fiber optical waveguide member in a stationary position within the guide means.

20. The apparatus of claim 14 further comprising fiber optical waveguide member advance interlock means, the interlocking means is for laser firing and fiber control that includes a distal heart contact member biased by a coaxial spring-biased electrical contact switch element that encompasses the at least one fiber optical waveguide member.

21. The apparatus of claim 14 further comprising tissue piercing means extending adjacent the distal end of the guide means.

22. The apparatus of claim 21 in which the tissue piercing means further comprises a heating means.

23. A hand surgical apparatus for securing a distal end of a laser delivery means operated from a remote laser device comprising:

a guide means defining a body having proximal and distal ends, the body having a length and width dimension no larger than a length and width dimension of the finger's of a surgeon's hand, the guide means: a) is connected to a finger mounting means, b) encompasses at least one fiber optical waveguide member which forms part of a laser delivery means and c) is adapted for directing laser energy outwardly from the distal end of the laser delivery means; and, a finger mounting means for attaching the guide means to one finger of the surgeon's hand, yet enabling movement of the finger, wherein the finger mounting means has a central axis;

the guide means and the finger mounting means further determining orientation of the distal end of the laser delivery means effectuated by movement of the at least one finger, thereby stabilizing and providing precision aiming of the laser delivery means for an internal surgical procedure.

24. The apparatus of claim 23 in which the finger mounting means comprises at least one generally circular ring portion for removably encircling the one finger of the surgeon's hand, the central axis substantially perpendicular to the circular ring portion.

25. The apparatus of claim 23 in which the guide means secures the laser delivery means to the one finger of the surgeon's hand in a direction parallel to the central axis of the finger mounting means.

26. The apparatus of claim 23 in which the guide means secures the laser delivery means to the one finger of the surgeon's hand in a direction at an angle to the central axis of the finger mounting means.

27. The apparatus of claim 23 in which the guide means is tubular with a preselected curvature.

28. The apparatus of claim 23 in which the guide means is tubular and adjustable so as to orient the laser delivery means axially with respect to the central axis and into a plurality of positions at an angle to the central axis.

29. The apparatus of claim 23 further comprising a locking means for coupling the laser delivery means to the guide means.

30. The apparatus of claim 29 in which the locking means comprises an O-ring and a cap portion.

31. The apparatus of claim 29 in which the locking means is a closure for coupling the laser delivery means to the guide means.

32. The apparatus of claim 23 in which the guide means is rotatably attached to the finger mounting means.

33. The apparatus of claim 32 in which the rotating guide means is indexed so as to orient the laser delivery means into a plurality of positions with respect to the central axis.

34. The apparatus of claim 23 further comprising a fiber advance means and interlocking means attached to the guide means, the fiber advance means includes a finger manipulable member for translation of the at least one fiber optical waveguide member.

35. The apparatus of claim 34 wherein the interlocking means is for laser firing and fiber control that includes a distal heart contact member biased by a coaxial spring-biased electrical contact switch element that encompasses the at least one fiber optical waveguide member.

* * * * *

UNITED STATES PATENT AND TRADEMARK OFFICE
CERTIFICATE OF CORRECTION

PATENT NO. : 5,693,041
DATED : December 2, 1997
INVENTOR(S) : Douglas R. Murphy-Chutorian It is certified that error appears in the above-indentified patent and that said Letters Patent is hereby corrected as shown below:

In claim 1, col. 9, line 28, change "finger's" to --fingers--.

In claim 23, col. 11, line 1, change "finger's" to --fingers--.

Signed and Sealed this

Tenth Day of March, 1998

Attest:

BRUCE LEHMAN

Attesting Officer

Commissioner of Patents and Trademarks